United States Patent [19]
Krishnan et al.

[11] Patent Number: 6,052,187
[45] Date of Patent: Apr. 18, 2000

[54] HYPERSPECTRAL POLARIZATION PROFILER FOR REMOTE SENSING

[75] Inventors: Shankar Krishnan, Chicago; Daniel Scott Hampton, Mundelein; Paul C. Nordine, Deerfield, all of Ill.

[73] Assignee: Containerless Research, Inc., Evanston, Ill.

[21] Appl. No.: 09/144,531

[22] Filed: Aug. 31, 1998

[51] Int. Cl.⁷ ...................................................... G01J 4/00
[52] U.S. Cl. ............................................ 356/364; 356/369
[58] Field of Search .................................. 356/364, 369, 356/351, 328, 73, 173, 318

[56] References Cited

U.S. PATENT DOCUMENTS

| | | |
|---|---|---|
| 3,504,975 | 4/1970 | White . |
| 3,910,701 | 10/1975 | Henderson et al. . |
| 4,052,666 | 10/1977 | Fletcher et al. . |
| 4,500,641 | 2/1985 | van den Engh et al. . |
| 4,517,456 | 5/1985 | Halsall et al. . |
| 4,560,275 | 12/1985 | Goetz . |
| 5,257,085 | 10/1993 | Ulich et al. . |
| 5,313,264 | 5/1994 | Ivarsson et al. . |
| 5,412,219 | 5/1995 | Chappelle et al. . |
| 5,467,271 | 11/1995 | Abel et al. . |
| 5,471,056 | 11/1995 | Prelat . |
| 5,483,066 | 1/1996 | Sadjadi et al. . |
| 5,507,115 | 4/1996 | Nelson . |
| 5,576,550 | 11/1996 | Koppikar . |
| 5,608,526 | 3/1997 | Piwonka-Corle et al. . |
| 5,661,817 | 8/1997 | Hatlestad et al. . |
| 5,764,819 | 6/1998 | Orr et al. . |
| 5,782,770 | 7/1998 | Mooradian et al. ................ 600/476 |
| 5,890,095 | 3/1999 | Barbour et al. ..................... 356/364 |

OTHER PUBLICATIONS

Kalshoven, et al.; Remote Sensing of Crop Parameters with a Polarized, Frequency–Doubled Nd: YAG Laser; *Applied Optics*; vol. 34, No. 15; May 20, 1995; pp. 2745–2749.

Kalshoven; Hyperspectral Low Altitude Flashtube Illuminator System For Visible and Near–Infrared Remote Sensing; Presented at the *Second International Airborne Remote Sensing Conference and Exhibition*, San Francisco, California; Jun. 24, 1996.

Cecchi, et al.; Fluorescence Lidar Remote Sensing of Vegetation, *SPIE*, v. 2585, (1996), pp. 48–56.

Barbini, et al.; Laser Remote Monitoring of the Plant Photosynthetic Activity, *SPIE*, v. 2585, (1996), pp. 57–65.

Savenkov, et al.; Polarization Properties of Some Kinds of Foliage Covers, *SPIE*, v. 2585, (1966), pp. 66–70.

*Primary Examiner*—Frank G. Font
*Assistant Examiner*—Roy M. Punnoose
*Attorney, Agent, or Firm*—Bullwinkel Partners, Ltd.

[57] ABSTRACT

A device to provide hyperspectral reflection spectrum, hyperspectral depolarization, and hyperspectral fluorescence spectrum data in a portable, remote sensing instrument. The device can provide a large range of remotely-sensed optical property data, presently only obtainable in laboratories, in a low-cost field instrument. Among its many uses, the present invention can be used by farmers as a tool for determining the nitrogen content of crops to optimize fertilizer laydown.

25 Claims, 3 Drawing Sheets

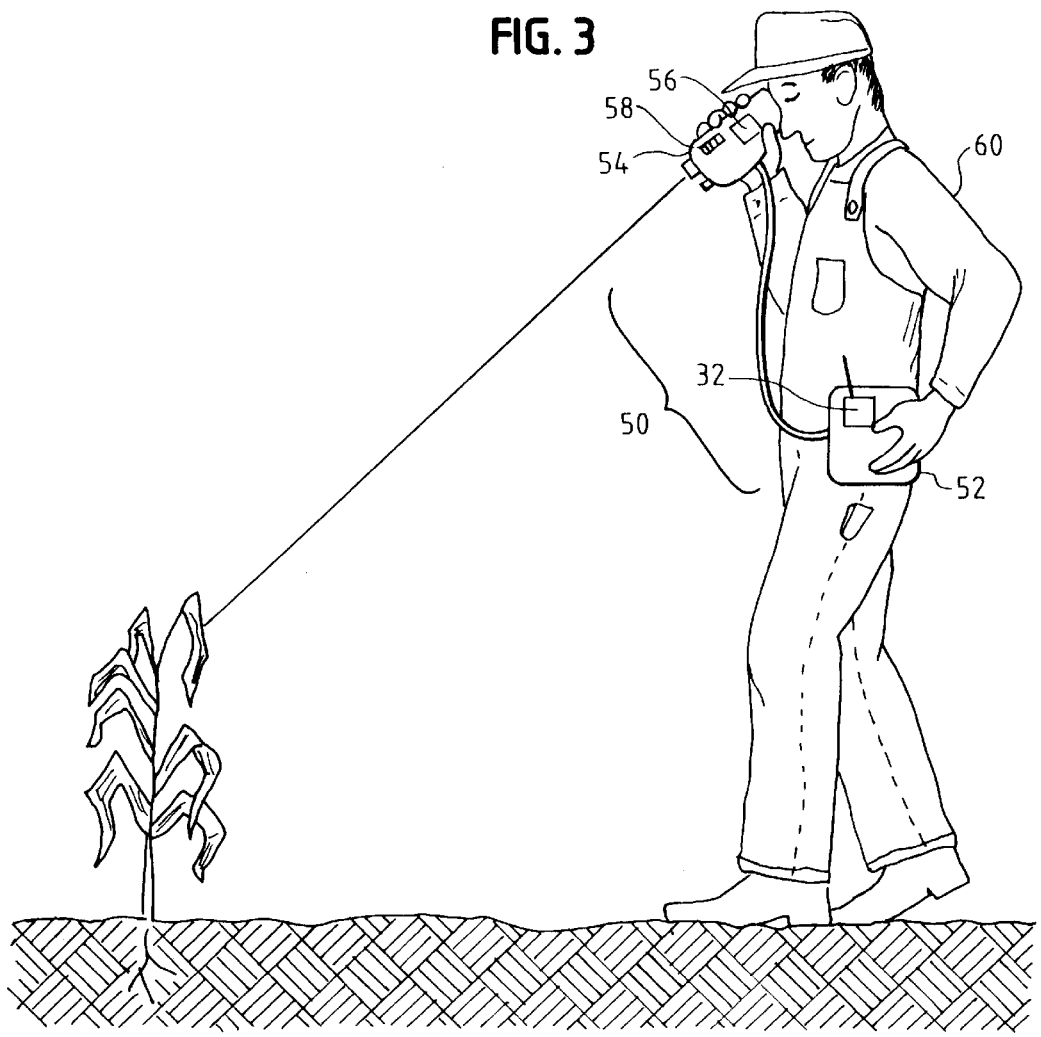

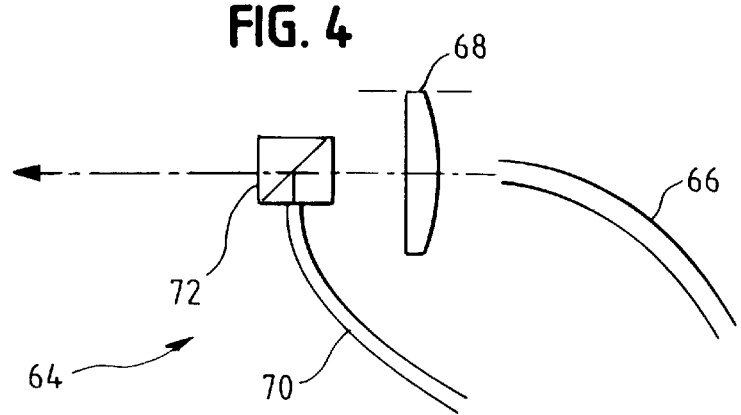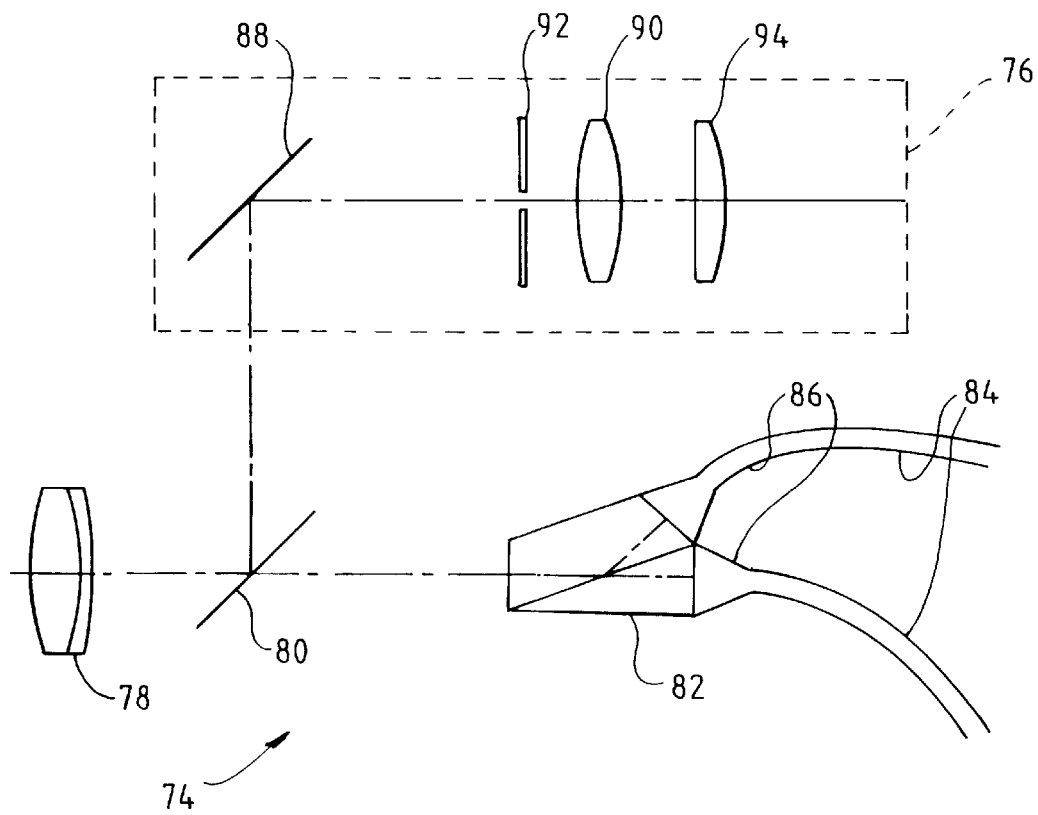

HYPERSPECTRAL POLARIZATION PROFILER FOR REMOTE SENSING

FIELD OF THE INVENTION

This patent relates to a device and method for the remote sensing of characteristics of a target object. More specifically, this invention relates to a device and method that exploits the different optical properties of objects, such as depolarization upon reflection, to deduce structural information related to characteristics of an object.

BACKGROUND OF THE INVENTION

Theory of Light Scattering from an Object

Polarimetry is the analysis of the polarization state of light. When polarized light (the "incident light") is directed onto an object, the depolarization upon reflection for the object can be directly measured. The depolarization which occurs upon reflection can be measured by splitting the reflected light into two orthogonally oriented states and calculating the signal ratios from two light sensitive detectors that view the orthogonally oriented light beams. The detectors, with separate polarization analyzers oriented perpendicular ($P^1$) and parallel ($p^2$) to the direction of polarization of the incident light, measure the reflected light. The degree of depolarization is given by:

$$\text{Depolarization}(p) = P^1/P^2 \quad (1)$$

This ratio always yields a positive value between 0 and 1. This equation is different from that used in passive (solar-based) measurements because of the partial polarization of sunlight.

Depolarization arises due to multiple scattering of light bouncing off an object, and its magnitude is a function of the surface texture and physiology (for plants). If the surface is smooth and reflection is very specular, no depolarization will occur. This is typical of many man-made objects. On the other hand, a lambertian surface will diffuse and depolarize the reflected light when the surface is even slightly rough. Cellular materials such as plants will depolarize backscattered radiation to a degree that depends on the relative amounts of specular reflection from the surface and the diffuse reflection from the interior of the material. For a light source with a divergence $\theta$ and energy E located at a distance h from a target surface, the specular component, $E_s$, of the backscatter is:

$$E_s = (p_s/16)(D_c/h\tan(\theta/2))^2 E \quad (2)$$

where $p_s$ is the specular reflectance and $D_c$ is the diameter of the collection optics. The lambertian backscatter energy, $E_1$, contribution to the total return signal is:

$$E_1 = (p_1/4)(D_c/h)^2 E \quad (3)$$

where $p_1$ is the fraction of the incident light that is diffusely scattered. $p_1$ can be assumed to be 20% for a general case. Egan and Hilgeman have measured the retroreflectance from numerous materials and have reported the backscatter enhancement, R, calculated as $p_s/p_1$, to range from 0.25 to >10 depending on the materials and the coherence of light.

Taking the ratio of Eqs. 2 and 3, the ratio of specular to diffuse retroreflectance is:

$$E_{ratio} = p_s/(4p_1\tan^2(\theta/2)) \quad (4)$$

Equation 4 shows that only the source divergence governs the backscatter enhancement of the signal. Equations 2 and 3 also provide a direct method to estimate the absolute energy of the return signal in the design of detector electronics and in the selection of light sources with sufficient power.

Wavelength Dependence of Light Scattering

The hyperspectral concept of the instant invention, particularly as it applies to the analysis of vegetation, takes advantage of the change in the reflection characteristics of leaves that occurs in the vicinity of 700 nm wavelength. Below about 700 nm, light is strongly absorbed by plant leaves and the depolarization of any scattered radiation is relatively small. Leaves usually reflect weakly in the blue and red wavelengths owing to absorption by pigments, and strongly in the infrared due to cellular refraction. At wavelengths longer than about 700 nm, the degree of depolarization is great due to multiple scattering effects which strongly depolarize the reflected light. Further, the degree of depolarization is species dependent and exhibits a characteristic wavelength dependence for each species because the leaf morphology and structure are characteristic to a particular species of plants.

Fluorescence and Vegetation Diagnostics

Radiation induced fluorescence signatures may be used to distinguish between stressed and healthy vegetation. In the instant invention, fluorescence effects can be uniquely studied by delivering only shorter wavelength radiation produced by a flashlamp to the target vegetation (by inserting a short pass filter in the output optical train) and measuring the fluorescent response from the vegetation at wavelengths longer that the wavelength of the delivered radiation.

Since fluorescent returns are small compared with the backscatter intensity, typically about 1% of the backscatter intensity, a higher collecting efficiency is required when operating in the fluorescence detection mode.

Plant stress can be directly related to the fluorescence signature. This has been demonstrated in the literature where the fluorescence signature of a stressed plant is compared with that from a healthy plant. It has been found that a healthy plant usually exhibits a peak in the fluorescence spectrum at 685 nm. On the other hand, a stressed plant shows a lowering of this peak, but a weaker peak at 735 nm increases in strength. These wavelengths are only nominal values; it is therefore useful to measure the fluorescence spectrum continuously. The ratio of the fluorescence at 685 nm to 735 nm is directly proportional to the plant health; the higher this value, the healthier the plant.

In the present invention, it is possible to measure radiation-induced fluorescence by allowing only the radiation from a flashlamp transmitted through a short-pass filter to strike the target. The instrument then measures the fluorescent response from the vegetation instead of the backscatter that would occur if the short-pass filter were not used.

DESCRIPTION OF THE RELATED ART

The depolarization of polarized light scattered from vegetation is known to be a function of a number of parameters, including moisture, fertilization levels, plant stress, mineral content, and other physiological parameters. Thus, depolarization may be used to study the state of a plant, and thus monitor its health. Clearly, the application of this type of measurement to crops has major commercial potential. A number of references are directed to methods and devices for the remote sensing of objects using electromagnetic radiation, most of which employ long distance sensing methods, eg. space or airborne sensors, or aerial boom mounted sensors.

Kalshoven et al. in *Applied Optics*, vol. 34, No. 15, pp. 2745–2749 (May 20, 1995) demonstrated that depolarization measured at 532 nm (visible) and 1064 nm (IR) is a function of nitrogen fertilization levels. Kalshoven describes mounting a polarization sensor to an aerial boom truck moving around a field to evaluate whether laser polarimetry could detect different plant physiologies resulting from the application of different nitrogen fertilizer doses in corn. Kalshoven reported that, in the infrared range, depolarization from corn increases with increasing nitrogen fertilization.

The method described in Kalshoven employs two electromagnetic wavelengths, i.e., one in the infrared spectrum and one in the visible, to measure depolarization from canopies. By contrast, the present invention can measure depolarization from individual leaves and single target surfaces. Moreover, the Kalshoven device is not portable (i.e. capable of being handheld) as is the present invention.

Kalshoven employs a division of wavefront design to obtain orthogonal polarization states of the collected light. By contrast, a division of amplitude design is used in the present invention. This difference is not important at the large distances employed by Kalshoven because the wavefront becomes highly uniform at large working distances, However, at smaller working distances such as those encountered when using the present invention, a division of amplitude design is preferred because the wavefront can be non-uniform, depending on the characteristics of the target object and the incident light beam. When a non-uniform wavefront occurs, reproducible and accurate measurements of the polarization state of light are not possible by a division of wavefront method. The division of amplitude technique employed by the present invention provides an additional benefit of simplifying the design of the optical and mechanical components to focus the light collecting system over a large range of working distances.

Savenkov and Marienko have shown that the degree of polarization signature from leaves is a function of the moisture content of leaves. Savenkov and Marienko employed single wavelength ellipsometric measurements with a single wavelength helium neon laser light source. Savenkov and Marienko's method requires a substantial angular separation of the incident and reflected light beams. Savenkov and Marienko's approach differs from the present invention in which hyperspectral measurements are obtained and the incident and reflected light beams are nearly coincident (allowing the light source and detector system to be contained in a single hand-held unit).

Sadjadi et al. U.S. Pat. No. 5,483,066 describes a system for identifying vegetation for the controlled application of chemicals to a field. The system uses a polarization-sensitive IR sensor connected to a "memory map" so that the image can be compared to stored data. If the image matches that of a stored map, the vegetation in the target field can be identified, and chemical spray heads can be activated. The Sadjadi system employs the polarization properties of light collected from vegetation for image recognition purposes, but it does not employ the polarization properties of the light to determine properties of the vegetation itself. Sadjadi does not determine or employ properties that require knowledge of the polarization state of the light incident on the vegetation.

Radiation-induced fluorescence from vegetation is a rich field, with numerous examples of its use to diagnose plant photosynthetic activity. One such example is that by Barbini et al., as reported in *Proc. SPIE*, 2585, 66 (1996). There it was shown that there is a shift in the fluorescence signature of a stressed plant compared to a healthy plant.

Orr et al. U.S. Pat. No. 5,764,819 describes a method for classifying plants for evaluating and breeding programs involving (1) taking high resolution infrared reflectance images of a group of plants at an elevation of about 150–200 feet using an aerial surveillance camera, (2) developing a descriptor by performing operations on the raw infrared data, (3) using the descriptor to classify the plants, and (4) selecting for future breeding purposes those plants that display a preferred phenotypic if characteristic. The method can be used, for example, to select from a number of test plots corn genotypes on the basis of yield performance. The Orr method uses a passive light source—the sun—although the use of an active light source is discussed. Orr et al. do not measure any polarization properties of the reflected light, nor does the Orr et al. method discern the cell structure of the target vegetation.

Fletcher U.S. Pat. No. 4,052,666 describes a method of remote sensing of vegetation by focusing microwaves onto a target at a predetermined angle and measuring the phase difference between the incident and reflected microwaves. The phase difference is caused by the intrinsic properties of the target vegetation, such as water content. The Fletcher method measures properties in the microwave band, in which the wavelength of radiation is too long to determine phenomena based on the plant cell structure.

The Need for a Portable Hyperspectral Polarization Profiler

Detection of fertilizer levels is important in farming practice. Fertilizers are expensive, and the practice of excess fertilization is coming under increasing scrutiny from many concerned parties due to the "run-off" of the excess fertilizer into rivers, streams, lakes and underground aquifers which can be harmful to fisheries, wildlife and humans. By remotely detecting the fertilizer levels, it would be possible for farmers to precisely control fertilizer levels, minimize "run-off" and its attendant health and environmental problems, and save money from not having to apply excess fertilizer (which is one of the most expensive crop inputs used in farming today).

It has been found that the depolarization of light scattered from vegetation is a function of the cell structure and physiological properties of the vegetation, which are in turn a function of environmental factors such as nitrogen fertilizer level, moisture level, and soil mineral content. Most present remote sensing methods do not use active light sources, cannot be carried by a human, employ long distance sensing methods, and/or typically employ a single electromagnetic wavelength to determine plant characteristics. Thus there exists a need for a portable device which uses an active light source to direct polarized light onto an object a short distance away to determine the object's characteristics (such as nitrogen level in corn plants) using multiple wavelength light sensors.

Thus it is an object of the present invention to provide a device and method for remote sensing a physiological characteristic of an object by measuring an optical property of light reflected from the object.

A further object is to provide a portable hyperspectral depolarization profiler with an active light source capable of creating light having a spectral content spanning at least 20 nm in wavelength for the remote sensing of vegetation.

A still further object of the present invention is to provide a non-invasive, remote polarization sensor to establish and control plant health and thereby increase crop yields.

A still further object of the present invention is to provide a hyperspectral polarization profiler that can be used at short distances.

Still further and additional objects will appear from the description, accompanying drawings, and appended claims.

SUMMARY OF THE INVENTION

The present invention is a method and device for the remote sensing of a physiological characteristic of a target object. The uniqueness of the present invention lies in the fact that it represents the first effort to provide hyperspectral polarization, reflectance, and fluorescence data in a portable, remote sensing instrument. The device can provide a large range of remotely-sensed optical property data in a low-cost field instrument. Among its many uses, the present invention can be used to determine nitrogen levels in crops, the fibrous cellular microstructure of trees, and the composition of minerals.

The device disclosed herein comprises means for polarizing light from a light source, means for directing the polarized light onto a target object, means for collecting the light from the target object, means for separating the collected light into two or more polarized components, means for measuring an optical property of the collected polarized light, and means for converting the optical property into data useful in determining a characteristic of the target object.

The light source may be active or passive. The light reflected back from the object is collected by an achromatic objective lens, mirror or other suitable light collection apparatus. In trials, a lens with an aperture having a radius of ½ inch and an F-number between 2 and 3 was used. The collected light is separated by a beamsplitter, polarized, and delivered to optical fibers that transmit the separate polarized components of the collected light to spectrometers.

The device comprises three main subsystems: light source delivery, optical collection and spectrometers, and data acquisition. The light source delivery subsystem includes the means for polarizing and directing light onto the target object. The optical collection and spectrometers subsystem collects the light from the target object and measures the polarization and intensity of the collected light as a function of wavelength. The data acquisition subsystem converts the raw optical data into useful information about the target object.

In one embodiment, the light source delivery and optical collection subsystems are contained within a single handheld optical unit. The spectrometer(s) are contained within a separate electronics unit, which may be connected by cable to a separate microprocessor (laptop). In a second embodiment, the light source delivery system and collection optics are contained within a hand-held optical unit, and the data acquisition subsystem is contained within a separate electronics unit which contains a dedicated microprocessor for the instrument operation and data acquisition, reduction and analysis functions, thus eliminating the need for a separate microprocessor. The device may be interfaced with a global positioning system receiving unit connected to a computer to provide the user with information regarding the location at which the measurements were made.

The optical properties of the collected light that may be used to determine the object's characteristics are its hyperspectral reflectance, degree of polarization, and fluorescence. These optical properties may be measured by a spectrometer capable of providing 10 nm spectral resolution at wavelengths from about 400 nm to about 900 nm and preferably from about 350 nm to about 1,000 nm.

The present invention has proved useful in determining the nitrogen content of corn plants by measuring the hyperspectral reflectance of light directed at the plant. Although the example disclosed herein was done using plants as the target objects, it is anticipated that the device and method disclosed and claimed herein will be useful in determining the characteristics of nonplant objects as well, including soil and minerals.

THE DRAWINGS

FIG. 1 is a schematic diagram of the device according to the present invention in which the light delivery and optical collection subsystems are located in a single handheld unit and the instrument operation and data acquisition, reduction and analysis functions are performed by a separate microprocessor (laptop).

FIG. 2 is a schematic diagram of a second embodiment of the present invention in which the optical instrumentation is located in a handheld optical unit and the instrument operation and data acquisition, reduction and analysis are performed by a dedicated microprocessor located in a separate but connected electronics unit.

FIG. 3 is a schematic diagram of the device of FIG. 2 1i being operated by a human in which the optical unit is handheld and the electronics unit is carried about the user's waist.

FIG. 4 is a schematic of the light delivery system of the device of FIG. 1.

FIG. 5 is a schematic of the optical collection system of the device of FIG. 1.

DETAILED DESCRIPTION OF THE INVENTION

Figure 6:
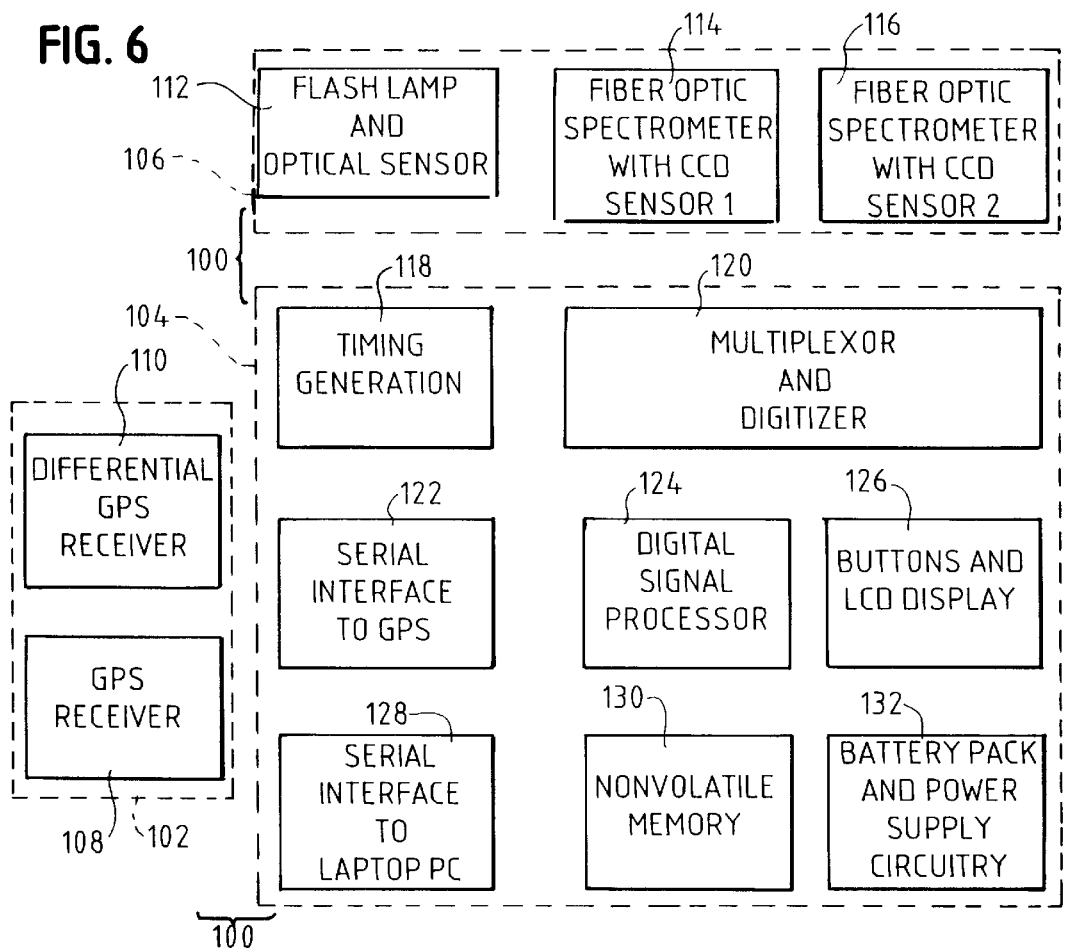
FIG. 6 is a schematic block diagram of the controller electronics of the device of FIG. 1.

For the purpose of this invention, the following definitions apply:

Active light source. A light source that is part of the instrument.

Backscatter. The scattering of radiation in a direction opposite to that of the incident radiation.

Hyperspectral. Spectra that are measured at two or more wavelengths with a spectral resolution of 10 nm or less where the separation between the wavelengths is greater than the spectral resolution.

Passive light source. A naturally occurring light source, such as the sun.

Portable. Easily carried by a human.

Remote sensing. Non-contact sensing.

General Description of HYPOP Instrument

Turning to the drawings, there is shown in FIGS. 1–3 two embodiments of the present invention, a hyperspectral polarization profiler (HYPOP) for the remote sensing of objects. The device comprises three main subsystems: light source delivery, optical collection and spectrometers, and data acquisition.

The light source delivery subsystem preferably comprises an active light source, a lens and a polarizing element. The active light source may be a flashlamp, laser, or other suitable light source. Alternatively, a passive light source (eg. the sun) may be used. If an active light source is used, the light source preferably should be capable of creating light having a spectral content spanning at least 20 nm.

The optical collection and spectrometers subsystem preferably comprises a collecting lens or mirrors, a first beamsplitter, viewing optics, a second beamsplitter, and one or more spectrometers. Preferably, the optical collection subsystem and the light source delivery subsystem are contained within a single handheld unit, referred to as an optical unit.

The data acquisition subsystem comprises a microprocessor for instrument operation and data acquisition, reduction and analysis functions. The microprocessor may be a separate laptop computer as in FIG. 1, or it may be contained within the electronics unit carried by the user as in FIGS. 2-3.

FIG. 1 is a schematic diagram of the device 10 according to the present invention in which the light delivery and optical collection subsystems are located in a single handheld optical unit 14 and the instrument operation and data acquisition, reduction and analysis functions are performed by a dedicated microprocessor 12 (laptop). The optical unit 14 contains the light delivery and optical collection systems, and has a light collection port 16 and measurement push buttons 18, 20. A separate electronics unit 22 contains at least one spectrometer 24, a battery 26 and a circuit card 28. A flashlamp 30 may be housed separately. An optional global positioning system device 32 may be connected to the laptop 12.

In this first embodiment the optical unit 14 is designed to be carried by the user. The electronics unit 22 is connected to the dedicated microprocessor 12 by a cable 34. The flashlamp 30 and electronics unit 22 are designed to be attached to a belt worn around the user's waist. A pair of cables 36, 38 connects these subsystems to the small hand held optical unit 14 that contains the light delivery system and its monitor detector, a single collecting port 16, a polarization-splitting element, short fiber cables, target viewing optics, a firing push-button 20, and external connectors.

In the second embodiment 50 of the invention shown in FIGS. 2 and 3, the electronics unit 52 contains a dedicated microprocessor for the instrument operation and data acquisition, reduction and analysis functions. The microprocessor and custom electronics unit 52 eliminates the need for a laptop in field measurements. The optional global positioning system 32 is shown located on the electronics unit 52.

The second embodiment adds some features to the optical unit 54, such as an LCD data display unit 56 and scroll buttons 58. The second embodiment is lightweight, portable, easy to use, and versatile (eg. may be mounted on a tripod).

FIG. 3 shows the conceptual design of the use of a HYPOP 50 by a human 60. The HYPOP is shown in two units: the optical unit 54 containing the light delivery and collection optics subsystems, and the electronics unit 52 containing the data acquisition subsystem, including the reflected light signal processing unit.

The present invention is capable of measuring depolarization as a function of wavelength from about 350 nm to about 1,000 nm, spectral reflectance curves, and radiation-induced fluorescence signatures. All of these optical properties are directly related to vegetation health and plant stress.

FIG. 4 is a schematic of the light source delivery subsystem 64 of the present device. The light source delivery subsystem 64 comprises a light source (not shown) for delivering light via a fiber optic cable 66, a movable lens 68, a second fiber optic cable 70 running from a reference detector (not shown) or a reference spectrometer (not shown) to a polarizing prism 72. The light source may be a flashlamp, one or more pulsed or continuous wave lasers that provide at least two wavelengths of light, or any other suitable light source. In initial tests a FlashPac™ model 1102 xenon flashlamp from EG&G was used. The model 1102 was selected on the basis of its suitability for use in a portable instrument. The ignition circuitry and xenon flashlamp were contained within a 6.7×1.3×3.4 (inch) housing weighing 15 oz. The unit required 12 V power and a TTL-compatible trigger input. The housing and circuitry were designed for minimum radiated and conducted noise normally associated with flashlamp discharge currents. The FlashPac™ included a mount that covered the lamp allowing a ⅛ inch diameter fiber bundle to abut directly against the borosilicate envelope. Other commercially available lamps may be used as an active light source as long as they deliver enough peak power, are sufficiently small, lightweight, and have low power consumption.

Tests were also performed using a model DGS 5903-L xenon flash lamp from EG&G-Heimann. This light source provided a higher energy flash than the FlashPac™ source, employing an electrical energy input of up to 100 joules compared with 0.35 joules for the FlashPac™ source. The light intensity from the FlashPac™ is suitable for operation in the field at a working distance of about 6 inches to about 24 inches between the hand held unit and the target vegetation. At a distance of about six feet between the hand held unit and the target vegetation, as might occur if the user is in the position shown in FIG. 3, a light source having an electrical energy input of about 3 joules would be suitable. The 100 joule light source is suitable for operation at much greater distances, which may be used if the unit is mounted on a tractor or other vehicle, or used for measurements on tree canopies from the ground.

The source light output may be focused onto a fiber bundle that is <¼ inch diameter, containing individual silica clad fibers of ≦0.55 NA. (Alternatively, the source may be contained within the handheld optical unit 54 and its output may be directly incident on the target of interest, thus eliminating the need for fiber optics.) The ends of the bundle may be contained within a stainless steel ferrule. The length of the fiber bundle is determined by ergonomic considerations. The output end of the bundle terminates a in cylindrical housing containing a small lens that can be axially translated for various illumination spot sizes. This housing can be permanently installed into the sensing head, with provisions for easy installation of the fiber bundle and user focusing. The final component in the light delivery chain is a calcite linear polarizer, chosen because of its broad spectral range, resistance to UV damage, and high extinction ($10^{-5}$). Also, dichronic sheet polarizers may be used.

A short-pass filter (not shown) may be included in the light source optics. The filter allows the user to select the spectrum for the outgoing light. If the short-pass filter is used, then the target is illuminated by shorter wavelength radiation only, and the HYPOP may be used to study the fluorescence excited by the shorter wavelength radiation.

FIG. 5 is a schematic of the optical collection system 74, showing the collection path inside the optical unit 54, including the collection optics, polarization discrimination and viewing optics 76. Light received by the collection subsystem 74 passes through an objective lens 78. The objective lens 78 may have a fixed focus, fixed field of view design or it may be designed to be focused by the user. Mirrors may also be used to collect the light.

The light passing through the objective lens 78 is then passed through a first beamsplitter 80, for viewing, and then a second polarizing beamsplitter 82 or a combination of a beamsplitter and dichroic sheet polarizers which results in two orthogonally polarized beams. These two beams are delivered to two individual spectrometers. The two outputs of the spectrometers are then used, with the results of instrument calibration experiments, to derive depolarization (ratio), spectral reflectance (sum), and fluorescence (sum with shortwavelength incident radiation).

The measured depolarization ratio does not require knowledge of the light source power. However, if an optional reference detector or reference spectrometer is employed, the reference detector or spectrometer can be used as a source monitor for calculation of other properties. This requires a fiber optic cable 70 or other suitable means to deliver light from the light source delivery subsystem to the reference detector or reference spectrometer. In the first embodiment, the system electronics supports a monitor input. In the second embodiment, the custom electronics package includes a channel for this reference detector input. The data from a reference detector is useful for the determination of target reflectance and overall system efficiency. The fiber or other means for delivery to the reference detector or reference spectrometer may be placed in the exit window path of a Glan-type prism that polarizes the source light as shown in FIG. 4. Other means, such as a non-polarizing pellicle beamsplitter, may also be used to select a portion of the light for reference measurements.

The polarizing beamsplitter 82 preferably is made from birefringement material. Calcite was chosen because of its extremely high polarization discrimination, high optical transmittance, and broad spectral range. A Glan Thomson prism is suitable for this task because of its large, wavelength independent beam separation. The horizontal polarization component is transmitted through the beamsplitter 82 and the vertical component is reflected at a 45 degree angle to the transmitted beams.

At the image plane of the objective lens in each polarization channel is a large core (1 mm diameter) fiber optic 84, such as that provided by Ocean Optics, Inc. These single fibers are the common silica clad type, having a numerical aperture of 0.22. There are at least two methods to route these fibers to the sensing unit containing the spectrometers. The first method is to place cylindrical mounts at the two image planes, such that the fibers can be removed and inserted easily into the sensing unit with a mechanism for reproducible positioning. A second method involves having short fibers permanently installed inside the sensing head, with a suitable connector for attaching separate long fibers to the spectrometers. In either case, the fibers are bound together and enclosed in a tough, but flexible, sheath.

FIG. 5 also shows a planar optical component such as a pellicle or flat glass beamsplitter 80 that diverts a small portion of the light converging from the objective lens 78 into a viewing path 76. The effect of this component on the polarization is accounted for in the calibration. The viewing path 76 comprises beam steering elements 88, a field lens 90, a reticle 92, and an eye lens 94. Registration of the reticle 92 and the two polarization channels is pre-aligned. As shown in FIG. 5, the viewed scene would be erect, but reversed left to right. The instrument may have an image reversing element (e.g., reflective or dove prism) to eliminate this reversion.

If a record of the illumination scene is desired, an optional small CCD video camera (not shown) may be used instead of a visual sight. The CCD array employed by the video camera may be placed directly at the reticle site. The video camera would require increased battery power as well as frame storage electronics, but allows the user to import the video image of the scene into the analysis software or to use a time-stamped and/or record number-stamped video image to be viewed on a VCR. The contrast of the illumination spot against the solar background can be enhanced by synchronizing a fast video camera shutter with the light output.

Calibration of the relative sensitivities of the parallel/perpendicular components of the received light and the spectral sensitivities can be achieved in one step by measuring the response from a spectrally uniform and diffusely reflecting target (e.g., barium sulfate or Spectralon). This requires an assumption that the target has completely diffuse and depolarizing reflection over the entire wavelength range. In order to check this assumption, a separate light source may be used to illuminate the light collection system directly, using a polarizing prism to set the plane of polarization at 45 degrees to the directions determined by the two polarization channels. This approach guarantees that at all wavelengths the incident intensities will be equal for both polarizations. The response of the HYPOP to the calibration measurements is absorbed into a calibration table or function which contains the sensitivities to both the spectral and polarization characteristics.

Measurements of the depolarization (DEP) are readily obtained from Eq. 1, which requires the ratio of the perpendicular to the parallel components. This can be done via the laptop 12 for the first embodiment (FIG. 1), and with the aid of a digital signal processor (DSP) in the second embodiment (FIGS. 2 and 3).

The HYPOP device should also include provisions for background subtraction. In practice, the background can be measured before and after each lamp flash. With the aid of spectral calibration targets, the spectral reflectance curves may also be obtained by adding the signals obtained from the two channels. Fluorescence signatures are obtained by adding the two channels together with the source set for shorter wavelength radiation only (by using the short-pass filter). Standard or custom software may be used to process the data to provide these desired properties. The background measurements are separately recorded in the first embodiment (FIG. 1). The second embodiment (FIGS. 2 and 3) provides the background corrected data.

The spectrometer and detection system shall now be described. The two 1 mm fibers 84 in the polarization channels in FIG. 5 and the fiber 70 for the reference spectrometer are connected to a small triple spectrometer (not shown) such as the model ST2000 unit provided by Ocean Optics, Inc. Performance specifications of the ST2000 unit are provided below.

In the first embodiment, the software which controls the standard Ocean Optics, Inc. product was modified and additional electronics were provided to generate suitable timing signals for coordinated measurements of the background, reference spectrometer, and reflected light intensities. Operation was tested on targets with known reflectance to verify accurate operation of the system. In the second embodiment, the acquisition board supplied by Ocean Optics, Inc. can be replaced by a custom DSP processor to achieve maximum flexibility over integration time, triggering, data readout, and storage, as well as permitting the acquisition of the reference detector levels.

The triple spectrometer arrangement provides better than 10 nm spectral resolution over the 350 to 900 nm range. The standard spectrometer 24 of the first embodiment (FIG. 1) gets its power supply and transmits its data across a cable 34 that interfaces to a PCMCIA A/D board that interfaces to the laptop computer 12. The software provides all analytical functions (background subtraction, depolarization calculations, etc.), file storage, and data display features.

The following are the specifications of the model ST2000 spectrometer and detection system:
Detector Specs
Detector: 2048-element CCD
CCD elements 2048×12.5 $\mu$m ×200 um
Well Depth 350,000 photons Sensitivity 86 photons/count
- 2.9×10–17 joule/count
- 2.9×10–17 watts/counts (for 1-second integration)
- 350–950 nm wavelength range Optics specs
Grating 600 grooves/mm
Slits 50 μm×1 mm
Order sorting Permanently installed Schott glass longpass filters filters
Resolution 10 nm FWHM
Stray Light <0.01% at 600 nm
<0.1%at 435 nm
Fiberoptic SMA 905 connector to single strand optical fiber connector (0.22NA)

The data acquisition subsystem for the second embodiment comprises a controller capable of stand alone battery operation to acquire and store spectrometer and GPS data from multiple shots (several hundred) on a single battery charge and transfer the data to a laptop or desktop PC when the device is brought back from the field.

A block diagram of the system electronics for the second embodiment is shown in FIG. 6. The system electronics is schematically illustrated in three modules: (1) A fiber spectrometer module, (2) a GPS module, and (3) A controller module. The fiber optic spectrometer module comprises a flash lamp and optical sensor which may be a reference detector or a reference spectrometer, and two fiber optic spectrometer modules with CCD sensor arrays and signal conditioning electronics.

The operation of the two spectrometers' CCD linear array sensors is synchronized with one unit acting as a master. The detectors used in these units may be Sony ILX511 2048-pixel CCD linear image sensors, or any suitable detector.

These units provide video bandwidth analog pixel data that can be clocked out of linear shift registers at rates up to 2 MHZ. The power consumption requirements are very modest at 5 volts and 102 milliamps for the master unit, and 5 volts 70 milliamps for the slave unit. The dynamic range of the sensors is such that a 12 bit digitizer is required for optimum use. Optional spatial and/or temporal averaging can improve this resolution up to 16 bits.

As shown in FIG. 6, an optional global positioning system (GPS) Module may be incorporated in the system. With respect to the first embodiment (FIG. 1), the GPS module 32 is laptop ready. In the second embodiment (FIG. 2), the GPS module 32 is integrated within the HYPOP electronics unit 52.

Global positioning systems (GPS) refers to a technique for using satellite signals and optional land based radio beacon signals to determine the position of an object in three dimensional space. Standard Positioning Service (SPS), with position accuracy of 100 m, based on a set of signals from 24 satellites is available free of charge worldwide, to all civilian users. The Precise Positioning Service (PPS), is reserved for military purposes. However, it is possible to improve the accuracy of SPS based units by the use of signals transmitted by land based radio beacons maintained by the U.S. Coastguard. The technique requires a radio receiver known as the Differential GPS receiver.

GPS technology has made rapid advances over the last few years, and several commercial enterprises provide cost effective compact, portable units for the use in mapping, navigation, and recreation, such as Trimble, Garmin, and Communication Systems International Inc. The technology is also available for system integrators in the form of small printed circuit board units that require power, an antenna, and a computer interface.

A typical GPS module requires a +5 volt power supply, has a coaxial connector for an antenna, and a serial interface for presenting the data to a computer. Differential GPS receiver modules can directly interface to a standard GPS unit and transmit error correction information for improved accuracy.

The Trimble Sveesix-CM3 is a compact (3.25"×1.83"×0.58") GPS module. Power consumption is 230 ma at +5 V volts. This unit is capable of interfacing to a differential GPS unit such as the SBX-2 OEM module from Communication Systems International to obtain improved positional accuracy of 2 to 5 meters. The SBX-2 is a compact (3"×241) unit with a power consumption of 150 ma at +5 volts.

The system controller electronics 100 for the second embodiment, depicted schematically in FIG. 6, comprises a GPS submodule 102, an optical and spectrometers submodule 104 and a controller submodule 106. The GPS submodule comprises electronics for a GPS receiver 108 and a differential GPS receiver 110. The optical and spectrometers submodule 104 comprises electronics for a flashlamp and optical sensor 112, a fiber optic spectrometer with CCD sensor 114 and a second fiber optic spectrometer with CCD sensor 116. The controller submodule 106 comprises timing electronics 118, a multiplexor and digitizer 120, a serial interface 122 to the GPS 102, a digital signal processor 124, buttons and an LCD display 126, a serial interface 128 to the laptop, nonvolatile memory 130, and a battery pack and power supply circuitry 132.

The functions of the controller submodule are to: (1) respond to user button presses and provide LCD display prompts; (2) control spectrometer timing to acquire background reading; (3) control flash lamp charging and triggering; (4) control spectrometer timing to acquire intensities of light produced by operation of the flashlamp; (5) process spectrometer readings; (6) obtain position data from GPS unit; (7) save multiple readings in non volatile memory; (8) conserve battery power by disabling unused modules; and (9) interface to a laptop PC for data download and parameter settings.

The heart of the controller submodule 100 is the digital signal processor (DSP) 124 such as that available from Analog Devices (ADSP2181). The data processing requirements are minimal and thus the DSP 102 is not required for raw computing power. It is primarily used as a fast real time controller for coordinating all timing activities. Most timing is accomplished in timing generation software thus permitting complete flexibility including user control of integration times, delays between flash lamp trigger and start of integration, and sampling rates.

Logic and any high speed timing functions not suitable for software control can be implemented in a field programmable gate array (Altera EPF8452AQ106). The front end video bandwidth signals from both the spectrometer CCD arrays may be multiplexed by the multiplexor (also called a "mux") and digitizer 120 into a single fast analog to digital converter capable of 12 bit resolution and 10 megasamples per second rate. This is adequate to multiplex and read both sensors at the maximum rate of 2 Msps (limited by sensor clock rates).

Processed readings from the spectrometers tagged with GPS data are saved in lithium battery backed non volatile memory (NVRAM) 130 which is part of the electronics board. The NVRAM 130 may be implemented using Dallas Semiconductor Smart Sockets with a real time clock feature. This permits the recordings of a time stamp for the readings.

The estimated power consumption figures are presented for the various subsystems in the table below:

| Subsystem | Power Consumption (Watts) |
|---|---|
| Flash Lamp (FlashPac ™) | 15.6 |
| Spectrometers (two) | 0.9 |
| GPS Receiver | 1.25 |
| Differential GPS Receiver | 0.75 |
| Mux and Digitizer | 0.5 |
| Digital Signal Processor | 0.5 |
| Memory | 0.1 |
| Timing and Serial Interface | 0.2 |
| Power Supplies | 2.0 |
| TOTAL | 21.8 |

Since the duty cycle of the flash lamp is small (charging the FlashPac™ requires less than one second at the power given above), it is not an important component of the overall power requirement. However, its charging rate does determine the current capability of the power supply. The GPS modules can be selectively turned off to further reduce power consumption. The mux and digitizer can be enabled a few milliseconds before data acquisition to permit settling time for the electronics. Thus it is possible to reduce the average power consumption by an order of magnitude or more.

Assuming a 12 volt battery with a 1 ampere hour capacity it is feasible to acquire several hundred readings over a period of 12 to 24 hours on a single full charge. The power circuitry can also be designed to accept a wall transformation adapter 12 volt source or an automobile +12 volt source for further flexibility in operation.

In the second embodiment, an embedded microprocessor on board the controller is responsible for stand alone operation of the device without the intervention of a separate microprocessor or a laptop PC. Software on the separate microprocessor or laptop can communicate with the controller to extract saved data, adjust operating parameters, and save the data in a format that is suitable for access by well-developed software programs (e.g., those provided by Ocean Optics, Inc. or others) that perform spectrum analysis. The embedded microprocessor is programmed by a separate microprocessor. The following is a list of commands that the controller may respond to across a serial link from the PC:

1. Report Configuration Parameters
   a. integration time
   b. delay from flash lamp trigger to integration
   c. spatial average size
   d. temporal average size
2. Set Configuration Parameters
3. Report Data Contents
4. Clear Data Contents If a high energy light source (relative to the FlashPac™) is employed, the larger current draw of the flashlamp may require a dedicated battery. This would have the added benefit of allowing complete physical and electrical separation of the flashlamp system from all other components, as the flashlamp generates large current and voltage spikes and radiated EMI. All other components can easily run from a single battery located in the electronics unit. In the first embodiment, the laptop computer 12 requires its own battery.

Figure 7:
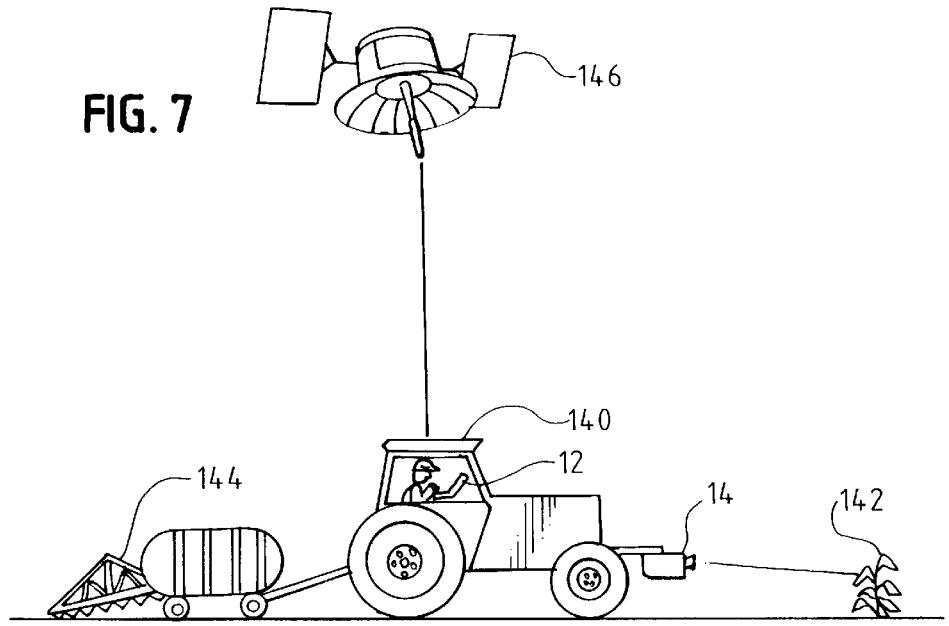
FIG. 7 is a schematic diagram of the device of FIG. 1 as it might be mounted to a tractor with the optical unit mounted to the front of the tractor and the electronics unit and microprocessor located in the tractor cab.

FIG. 7 shows the present invention as it might be used on a tractor 140 to precisely control the application of nitrogen fertilizer to a corn crop. The optical unit 14 is mounted to the front end of the tractor 140 and aimed at one or more corn plants 142. The tractor operator sits inside the tractor cab where a dedicated microprocessor 12 is located. The hyperspectral polarization profiler system senses the optical properties of the corn plants 142, determines the nitrogen level of the plants 142 based on these optical properties, and specifies the amount of fertilizer to be applied by the fertilizer sprayer 144 attached to the tractor 140 as it passes over the sensed plants 142 a moment later, taking into account the speed of the tractor 140 and the distance between the sensed plants 142 and the applicator 144. By employing an optional GPS system operating using multiple GPS satellites 146, the operator can determine the precise locations in the filed at which fertilizer was sprayed.

EXAMPLE

The first embodiment of the present invention underwent field testing at a farm near Rossville, Ill. in July 1998. The field contained rows of corn divided into five areas with different levels of applied nitrogen fertilizer. There were two separate plantings, one in May (early) and one in June (late). Each planting consisted of twelve rows of plants about 750 feet in length. The spacing between the rows was thirty inches, and the spacing between the two groups was about eight feet.

The corn that was planted in May was on average about three feet tall. The corn planted in June was on average about 8–12 inches tall. The May corn had about 12–18 leaves per plant while the June corn had about 7 leaves per plant. The residual soil nitrogen level was estimated to be about 40 lbs/acre from the previous year's soybean crop. Both May and June groups had been dressed with differing amounts of added nitrogen, arranged in a non-sequential manner. The added fertilizer amounts were zero, 70, 150, 200, and 250 lbs/acre. For this farm under these crop rotation conditions the optimum added fertilization level is considered to be approximately 170 lbs/acre.

Depolarization (DEP) was plotted versus average intensity for the 540–560 nm waveband where a maximum in depolarization was observed. Significant scatter in the intensity and depolarization values was observed, even though the incident light intensity was more or less constant for all of the measurements. The plots show minimal scatter at the higher intensities and considerable scatter at the smaller intensities.

The reflected light can be considered to have two components which are:

1. Light returned by specular reflection from the leaf surface layer which remains fully polarized, i.e., for which DEP=0; and
2. Light returned by multiple reflection by the internal structures, which is diffuse and highly depolarized, i.e., for which DEP is quite large.

The relative amounts of the two components can vary with geometric factors. The primary geometrical effects are:

1. Specular reflection that occurs in a cone-shaped volume whose orientation depends on the angle of incidence; and
2. The cone angle for specular reflection which depends on the curvature of the structures near the leaf surface, and varies with the size and shape of cells near the leaf surface.

The intensity of the specular component is independent of distance if the cone of specular reflection is completely within the instrument aperture. The intensity decreases with the square of distance if the cone is larger than the instrument aperture and centered on the aperture. The intensity decreases if the specular cone is larger than the instrument aperture and not centered on the aperture. Sensitivity to specular angle decreases with the magnitude of the cone angle. The intensity of the specular component approaches zero if the angle of incidence exceeds the cone angle. The intensity of the diffuse component decreases with the square of distance and is insensitive to small variations of the incidence angle.

The incidence angle and distance to the leaf surface were not precisely controlled, but gross variations in the values of these parameters did not occur. Thus, it appears that the cone angle for specular reflection is relatively small, but large enough to exceed the angle subtended by the instrument aperture. Also, the scatter in DEP values and in the intensity was primarily due to variations in the efficiency with which specular light was collected.

The light received from the plants was focused through a dielectic cube prism serving as a beamsplitter to two separate fiber optic receivers. The beamsplitter polarized the light over the desired spectrum with a 4:1 extinction. Since it is necessary to achieve 12 bit extinction, dichroic sheet polarizers were added to the exit faces of the prism.

Since the source and receiver optics were slightly displaced in this example, a plane of incidence was defined and the naming of the two light signal paths follows convention. Light that is polarized in the plane of incidence was denoted as "P" light, and light polarized perpendicular to the incident plane is denoted as "S" light. Measurements of raw voltages obtained from the spectrometer during the field test were plotted against wavelength for the P and S polarized components. The source was P-polarized so that the P component was always greater than the S component. The larger the difference, the smaller the depolarization.

The raw data were corrected for the relative sensitivities derived from the calibration procedure, and for the spectral sensitivities. The sum of the P and S intensities was proportional to reflectance. The reflectance was obtained by normalizing this sum by the signal obtained from a flat target which displayed a uniform spectral reflectance to give a smoothed reflectance curve for the plant.

For the early planting case, the depolarization (DEP=S/P) was calculated for five different fertilization levels. The following table lists the minimum DEP values as a function of fertilizer level:

TABLE 1

Minimum DEP Value as a Function of Added Fertilizer Level

| Added Fertilizer Level, lbs/acre | Early Planting | Late Planting |
|---|---|---|
| 0 | 0.41 | 0.23 |
| 70 | 0.23 | 0.23 |
| 150 | 0.18 | 0.19 |
| 200 | 0.22 | 0.23 |
| 250 | 0.28 | |

These data indicate that the measurement of DEP with the present invention is sensitive to nitrogen fertilizer level in young corn plants. Strong depolarization differences were easily seen in the early planting case, but not observed in the late planting case.

The results suggest the following interpretation for the timely detection of nitrogen uptake. Very young corn plants do not appear to require added nitrogen when there is some residual nitrogen present in the soil from the previous year's soybean crop. However, as the plants grow beyond the seven leaf stage the need for nitrogen increases, and at 6–8 weeks after planting, there are significant differences in the depolarization spectra for corn plants fertilized to different levels.

The uniqueness of our invention lies in the fact that it represents the first effort to provide hyperspectral polarization, reflectance, and fluorescence data in a portable, remote sensing instrument. The device provides a large range of remotely-sensed optical property data, presently only obtainable in laboratories, in a low-cost field instrument. Among its many uses, the present invention can be used to determine nitrogen levels in crops, the fibrous cellular microstructure of trees, and the composition of minerals.

Other modifications and alternative embodiments of the invention are contemplated which do not depart from the spirit and scope of the invention as defined by the foregoing teachings and appended claims. It is intended that the claims cover all such modifications that fall within their scope.

We claim as our invention:

1. A device for the remote sensing of a characteristic of a target object comprising:

means for polarizing light emanating from a light source;

means for directing the polarized light onto the target object;

means for collecting light from the target object;

means for separating the collected light into at least two polarized light beams;

means for measuring an optical property of the collected polarized light beams selected from the group consisting of hyperspectral reflection spectrum, hyperspectral depolarization, and hyperspectral fluorescence spectrum; and means for converting the optical property into data useful in determining a characteristic of the target object.

2. The device of claim 1 further comprising a light source.

3. The device of claim 2 in which the light source is one or more lasers which produce at least two discrete wavelengths of light.

4. The device of claim 2 in which the light source is a laser which produces continuous-wave radiation.

5. The device of claim 2 in which the light source is a plurality of pulsed lasers.

6. The device of claim 2 in which the light emanating from the light source passes through a short-pass filter to illuminate the target object with shorter wavelength light to induce fluorescence in the target object.

7. The device of claim 1 wherein the means for directing the polarized light onto the target object and means for collecting light from the target object are contained within a single handheld unit, thus rendering the unit portable.

8. The device of claim 1 wherein the means for separating the collected light comprises a polarizing beamsplitter made from birefringement material.

9. The device of claim 1 wherein the means for separating the collected light comprises a beamsplitter and dichronic sheet polarizers.

10. The device of claim 1 wherein the means for measuring an optical property is a spectrometer capable of providing 10 nm spectral resolution over a range of about 350 nm to about 1,000 nm.

11. The device of claim 3 wherein the target object is a corn plant, the optical property is hyperspectral depolarization and the characteristic is nitrogen content.

12. The device of claim 1 wherein the device interfaces with a global positioning system receiving unit connected to a computer to provide the user with information regarding the location of the target object.

13. A portable device for the remote sensing of physiological characteristics of plants comprising:

an active light source;

means for polarizing light emanating from the light source;

means for directing the polarized light onto a target plant of interest;

means for collecting light reflected back from the target plant of interest;

means for separating the collected light into at least two polarized components;

means for measuring an optical property of the collected light selected from the group consisting of hyperspectral reflection spectrum, hyperspectral depolarization, and hyperspectral fluorescence spectrum; and means for converting the optical property into data useful in determining a physiological characteristic of the target plant.

14. An apparatus for applying a corrective factor to a field of target objects comprising:

a vehicle;

the device of claim 1 carried by said vehicle to scan target objects along the path of said vehicle for determining a characteristic of said target objects;

means for comparing the detected characteristic of said scanned target objects with a predetermined desired level of such characteristic; and means mounted on such vehicle for controllably applying a corrective factor to said scanned target objects in response to the difference between said detected characteristic and said desired characteristic.

15. An apparatus for applying specific measured amounts of fertilizer to growing plants in an agricultural environment comprising:

a self-propelled agricultural vehicle;

the device of claim 11 mounted on said vehicle to scan plants for their nitrogen content;

means for comparing the detected nitrogen content with a predetermined desired level of such nitrogen content; and means mounted on such vehicle for controllably releasing a measured quantity of nitrogen fertilizer over said scanned plants in response to the difference between said detected nitrogen content and said desired nitrogen content.

16. A method for sensing a physiological characteristic of a target object comprising:

directing polarized light from a light source onto the target object;

collecting light reflected back from the target object;

separating the collected light into at least two polarized components;

measuring an optical property of the collected polarized components; and converting the optical property measurement into data useful in determining a characteristic of the target object.

17. The method of claim 16 wherein the light source is an active light source capable of creating light having a spectral content spanning at least 20 nm in wavelength.

18. The method of claim 16 wherein the target object is a plant and the active light source is capable of creating light having a spectral content from about 400 nm to about 900 nm in wavelength.

19. The method of claim 16 wherein the target object is a plant and the active light source is capable of creating light having a spectral content from about 350 nm to about 1,000 nm.

20. The method of claim 16 wherein the optical property is selected from the group consisting of hyperspectral reflection spectrum, hyperspectral depolarization, and hyperspectral fluorescence spectrum.

21. The method of claim 20 wherein the target object is a corn plant, the optical property is hyperspectral reflectance and the characteristic is nitrogen content.

22. The method of claim 16 wherein the target object is a tree and the characteristic is fibrous cellular microstructure.

23. The method of claim 16 wherein the characteristic is mineral composition.

24. A method for applying a corrective factor to a field of target objects comprising:

carrying the device of claim 1 on a vehicle along a pre-selected path relative to a field target objects, while continuously determining a characteristic of said target objects;

comparing the detected characteristic of said scanned target objects with a predetermined desired level of such characteristic; and applying a corrective factor to said scanned target objects in response to the difference between said detected characteristic and said desired characteristic.

25. A method for continuously applying specific measured amounts of fertilizer to growing plants in an agricultural environment comprising:

carrying the device of claim 11 on a self-propelled agricultural vehicle on a pre-selected path through a field of growing plants while scanning said plants for their nitrogen content;

comparing the detected nitrogen content of said scanned plants with a predetermined desired level of such nitrogen content; and applying a measured quantity of nitrogen fertilizer over said scanned plants in response to the difference between said detected nitrogen content and said desired nitrogen content.

* * * * *